United States Patent [19]
Ostrow

[11] Patent Number: 5,983,134
[45] Date of Patent: Nov. 9, 1999

[54] ELECTROPHORETIC CUFF APPARATUS DRUG DELIVERY SYSTEM

[75] Inventor: Alvin S. Ostrow, Ra'anana, Israel

[73] Assignee: Electromagnetic Bracing Systems Inc., Secaucus, N.J.

[21] Appl. No.: 09/096,469

[22] Filed: Jun. 12, 1998

Related U.S. Application Data

[63] Continuation-in-part of application No. 08/636,406, Apr. 23, 1996, Pat. No. 5,823,989
[60] Provisional application No. 60/049,446, Jun. 12, 1997.

[30] Foreign Application Priority Data

Apr. 23, 1995 [IL] Israel ........................................ 113459

[51] Int. Cl.⁶ .................................................. A61N 1/30
[52] U.S. Cl. .............................. 604/20; 604/67; 607/148; 607/149; 607/152; 607/153
[58] Field of Search .................. 604/20–21, 67; 607/152–153, 148–149

[56] References Cited

U.S. PATENT DOCUMENTS

| | | |
|---|---|---|
| 4,729,377 | 3/1988 | Granek et al. . |
| 4,968,297 | 11/1990 | Jacobsen et al. . |
| 5,037,380 | 8/1991 | Jacobsen et al. . |
| 5,823,989 | 10/1998 | Ostrow . |

FOREIGN PATENT DOCUMENTS 193480   9/1986   European Pat. Off. .

*Primary Examiner*—Mark Bockelman
*Attorney, Agent, or Firm*—Edward Langer

[57] ABSTRACT

A flexible cuff for wrapping around a part of a limb, that is comprised of multiple biosensing patch units of a required size and shape to fit the body contour for applying to an area of skin. The cuff has an array of flexible porous (polymer) electrodes held at constant potential with alternating polarities. A network of supply tubes connected to an external liquid reservoir provides a slow supply of medicated fluid to each electrode. A pump/titration regulator is in communication with the transdermal electrode to regulate permeant flow to the skin. An electric and an electromagnetic field applied through the cuff then causes the drug to be rapidly absorbed throughout the skin. The electrodes within the cuff, or the applicator pads which it is comprised of, can be additionally used for applying electromagnetic, Transcutaneous Nerve Stimulation, and for Electrical Muscle Stimulation. Alternatively, the cuff can be used to assist rehabilitation exercise therapy conditioning in combination with Electrical Muscle Stimulation.

20 Claims, 6 Drawing Sheets

ELECTROPHORETIC CUFF APPARATUS DRUG DELIVERY SYSTEM

CROSS-REFERENCE TO RELATED APPLICATIONS

The present invention is a continuation-in-part of U.S. patent application Ser. No. 08/636,406 filed Apr. 23, 1996 by the same inventor, entitled "Electrophoretic Cuff Apparatus Drug Delivery System" now U.S. Pat. No. 5,823,989; and claims the benefit of U.S. provisional patent application No. 60/049,446, filed Jun. 12, 1997.

FIELD OF THE INVENTION

The present invention relates generally to medical appliances and especially to the application of a uniform system of an electrophoretic pharmaceutical delivery cuff apparatus system where electrically charged porous pads are in fluid communication with a drug medium.

BACKGROUND OF THE INVENTION

Patients are often required to wear casts or braces over long periods of time. This limits access to the treatment area and prevents medical treatment. Atrophy of the underlying muscle tissue is a common problem. Because of the inaccessibility of the treatment area, drug delivery is made difficult, and traditional methods of drug delivery by injection must be used.

The use of iontophoresis and electrotherapy for drug delivery has been known and recognized as an acceptable form of treatment. Prior devices utilizing iontophoresis and/or electrophoresis were unable to simultaneously treat large areas systematically in an anatomical circumference or be incorporated under casts or braces, with the exception of the inventor's previous U.S. Pat. No. 5,344,384.

Furthermore, the previously known devices did not provide the availability of multiple treatment protocols.

Many iontophoretic drug delivery devices have been described in the patent literature, including U.S. Pat. Nos.:
5,387,189 to Gory et al;
5,358,483 to Sibalis;
5,356,632 to Gross et al;
5,312,325 to Sibalis;
5,279,544 to Gross et al;
5,167,479 to Sibalis;
5,156,591 to Gross et al;
5,135,479 to Sibalis et al;
5,088,977 to Sibalis;
5,057,072 to Phipps;
5,053,001 to Reller et al;
4,942,883 to Newman;
4,752,285 to Patelenz et al;
4,734,090 to Sibalis;
4,731,049 to Parsi;
4,622031 to Sibalis;
4,325,367 to Tapper; and
4,164,226 to Tapper.

The need to provide a broad spectrum of treatment protocols suited to the injury and/or medical condition of the patient requires a system having a high degree of drug flow controllability.

Controlled delivery of drugs through the skin by use of transdermal patches is well known in the prior art. Passive transdermal drug delivery patches provide advantages over other drug delivery methods by delivering the drug directly to the affected area. This method is advantageous over other known methods such as oral administration which necessitates absorption through the digestive tract, or intravenous drug administration which involves needles. Currently, certain patient types present serious problems to traditional IV techniques. These patients include: patients with blood disorders, immuno-compromised patients, patients with renal dysfunction, patients with vein disorders or deep set veins and small children. It is estimated that patients in the above categories represent at least 20–25% of all hospital patients. Both oral and intravenous administration involve administering high doses of drug to the body at one time, systemically affecting the whole body with the pharmaceutical. These high levels of drug concentration in the blood can create toxic side effects. In addition, only a very small percentage of the drug reaches the affected target area in the body.

There has been a trend toward demands for new methods of self-administered prescription pharmaceuticals such as time-release oral medications and transdermal patches. Transdermal delivery provides medication specifically to the area of treatment in the exact quantities required. However, the number of passive transdermal drug delivery patches available, such as the nicotine, estrogen and nitroglycerine patches, are limited because they are effective only with small-molecule drugs. Many of the newly developed proteins and peptide drugs are too large to be delivered through passive transdermal patches, forcing pharmaceutical companies to seek advanced delivery technology such as electrical assist (ionotophoresis) for large-molecule drugs.

Iontophoresis is a technique employed for enhancing the flux of ionized substances through membranes by application of electric current. The principal mechanisms by which iontophoresis enhances molecular transport across the skin are (a) repelling a charged ion from an electrode of the same charge, (b) electroosmosis, the convective movement of solvent that occurs through a charged pore in response the preferential passage of counter-ions when an electric field is applied or (c) increase skin permeability due to application of electrical current.

Many drugs have been formulated for commercial use in the pharmaceutical industry employing iontophoresis. Both passive and electrical assist transdermal drug delivery necessitate wearing transdermal patches made of synthetic substances consisting of a high co-polymer content for long periods of time, often causing skin reactions due to the body's rejection of the membrane as being foreign to the skin. Also, most membrane patches require a specific drug designed toward use with a particular membrane for a specified limited time of usage.

Therefore, it would be desirable to overcome the above-mentioned disadvantages and provide a transdermal active drug delivery system that would deliver large-molecule drugs in an efficient manner directly to the affected site, even under a cast or brace, while allowing long term skin contact without causing skin irritation.

OBJECTS OF THE INVENTION

Accordingly, it is a principal object of the present invention to overcome the disadvantages of prior art devices and systems and provide an electrophoretic cuff apparatus of the general character described herein which is not subject to the aforementioned deficiencies.

Another object of this invention is to provide an electrophoretic cuff apparatus that can fit under a cast or brace. A foam fabric can be used on the superior external surface of the apparatus, adding to patient comfort.

A further object of this invention is to provide an electrophoretic cuff apparatus having selective curative regimens that can be applied severally or together.

Another further object of this invention is to provide an electrophoretic cuff apparatus can be worn comfortably by the patient, as a lightweight, portable device that is cost effective to manufacture.

Another object of this invention is the capability to deliver any drug in a fluid medium having either a positive or a negative molecular valence through the skin, iontophoretically.

Many drugs have been formulated for use in iontophoretic systems, and others are being experimented with and developed by the pharmaceutical industry for the feasibility of their delivery via iontophoresis for commercial use (e.g., nicotine, antihistamines, beta-blocker, calcium channel blockers, non-steroidal, anti-inflammatory drugs, contraceptives, anti-arrhythmic drugs, antivirals, hormones, alpha-interferon and chemotherapeutic anti-cancer agents). Therefore, it is also an object to incorporate porous membranes having pores that can accommodate molecular drug weights from one to 50,000 Daltons, or greater.

Yet another object of this invention is to optimally produce a selected alternating positive and negative electrical charge from a controlled power source/console switch, thereby creating the electrical field polarity which is responsible for providing the "ionic drive" mechanism needed to modulate either anode or cathode drug delivery within the electrode applicator pads. The ionic drive mechanism is the force behind the electrochemical phenomenon of iontophoresis required to propel, infuse and deliver a pharmaceutical medium in accordance with its polar molecular valence through the surface of the skin by means of electroosmosis. The success of administering the fluid medium depends on the negative or positive valence of that medium for anode or cathode delivery.

It is another object that the invention can provide electromagnetophoresis. Scientific information supports the concept that electromagnetic fields (EMFs), in combination with drug delivery, can either increase the osmotic penetration of drugs through the skin known as "magnetophoresis", or that EMFs may help accelerate the effectiveness of exogenous drugs after being introduced into the body by transdermal or hypodermic methods. Exposure to PMF (Pulsed Magnetic Field) immediately after administration of methotrexate or mitomycin C, pharmaceutical anti-tumor agents, into the cell increases eddy current stimulation induced by PMF, and the cell cycle shifts from the non-proliferative to proliferative phase, resulting in increased anti-tumor activity.

It is another object of to provide combined therapy, there the combination of magnetotherapy, electrotherapy and iontophoresis heighten the effectiveness of electrochemotherapuetic treatment to a target area used for electrochemotherapy (ECT). The combination of multiple drivers to produce an electro-chemotherapeutic effect is known as "electro-infusion".

It is also another object of the invention to provide a membrane electrode with a biosensing component that can detect flow rate over time and the amount of permeant flow through the skin and the membrane as a component part of the titration, pump and/or siphon flow regulator system for the control of any number of drug permeants, severally, or in combination.

Another object of the invention is to create a membrane electrode with a layered structure comprising:

1. a microtitration foam layer in contact with the electrophoretic tubing that supplies the permeant superior to the electrode. This foam layer is intended to prevent leakage or seepage, and to ensure slow feed of the permeants traversing the porous membrane layer below; and
2. a porous electroconductive membrane layer or membranes with electroconductors; and
3. a biosensor or biosensors interconnected with the transdermal membrane junction to the skin which are placed as to allow the permeation of pharmaceutical fluids.

It is also an object of this invention to create a variety of configurations for constructing the cuff, whereby the cuff is constructed by the interconnecting of the membrane electrodes, or can be constructed merely as a housing matrix for the electrodes.

SUMMARY OF THE INVENTION

The electrophoretic cuff apparatus of the present invention encompasses the construction of a preform applicator wrap for applying an electrical current to electrophoretically porous, electrically conductive applicator pads to pass a slow drip liquid drug medium through the skin and surface tissues. The applicator wrap is externally self-supported, contiguous to a body surface to form a preform wrap or cuff.

In particular, the present invention concerns an electrotherapy apparatus incorporated within or without a cast or orthotic brace or preform that delivers ancillary treatment modalities which are provided by an optional Neuromuscular Electrostimulation, Transcutaneous Nerve Stimulation (T.E.N.S.) and Interferential Electrotherapy component. The preform forms a "cuff" that can be wrapped around the body in different sizes and sections for easy treatment of large and small anatomical areas. The cuff is connected to a Velcro attachment to latch on the sections connected by male and female electrical and fluid flow connectors respectively, to deliver the fluid medium and electrical charge.

The construction of the apparatus is important for regulated consistent uniform drug therapy around the circumference of a body part to increase efficiency of drug therapy application. Biosensors and a pump regulated titration system ensure precise regulation of drug flow transdermally through the skin and the transdermal membrane electrodes that act as a conduit reservoir for the flow of medicated permeants being supplied by a continuous source reservoir.

In addition to the application of electric energy in the present invention, a pulsed or continuous electromagnetic field is created by a separate circuit. When a medicament is added to the aqueous environment, the invention becomes a drug delivery apparatus with a variety of protocols for iontophoretic and electromagnetophoretic delivery systems.

When the apparatus is not used for drug delivery, it can be applied and worn while the patient is exercising or conducting the activities of daily living.

The cuff wrap matrix is formed of waterproof, molded and flexible plastic, Styrofoam or canvas-like material with male and female electrical and fluid flow connectors to accommodate a continuous hook-up for additional preform patches of various sizes and shapes, as required, to encompass the circumference of a desired target treatment area, thereby creating a "cuff" or wrap around any anatomical body part.

The wrap is provided with a network array of electrically conductive porous polymer membrane electrode applicator pads providing a "checkerboard" pattern of alternating positive and negative polarities.

The porous polymer electrode applicator pads can be energized by galvanic and electromagnetic current drivers to propel permeant drugs through means of either iontophoresis, magnetophoresis or combined electromagnetophoresis.

A feature regarding the present invention of the electrophoretic cuff is that it can have multiple uses beyond its use for introducing drugs transdermally. Thus, the present invention provides, in a versatile fashion, a variety of therapeutic benefits and applications with electrical energy modes for nerve stimulation, pain sedation and the prevention of atrophy. Additionally, when configured as a therapeutic garment, the mode of Electrical Muscular Stimulation (EMS) can be introduced during physical therapy exercises, weight training for neurologically impaired and atrophic muscles, etc.

It should be apparent that the multi-modal nature of this apparatus covers a broad spectrum of treatment protocols, including the treating of injuries to soft tissues, as well as arthritis of joints at selected locations of the human and mammalian bodies.

The cuff provides a consistent supply of medication by titration throughout the porous polymer membrane electrode applicator pads, to bathe the body part in a continuous fluid within a circumference, whereas other electrical transdermal drug delivery methods are not as easily accessible or applicable. This system also allows for transdermal drug treatment simultaneously to more than one location where medical attention is needed. In addition, a non-medicated fluid can also be used to moisten the porous electrodes as an electrolyte, to assist electrical conductivity when the apparatus is being used for purposes other than drug delivery.

In addition, the cuff applies continuous fluid medium from an external reservoir similar to intravenous (I.V.) applicators, but without the use of a syringe. The cuff can be used as an option to replace traditional methods of postoperative analgesia, such as intramuscular injections. The cuff has benefits for those patients who dislike needle injections—especially children.

Furthermore, the delivery of drugs transdermally is regulated and monitored through a computer chip and "pump" administration system that records the titration rate, amount and dosage of medication supplied. The pump can vary the speed of introduction of the transdermal permeant at a desired rate.

The pump administration and titration mechanisms are interactively connected to biosensor detection sensors located within the transdermal membrane electrode applicator pads. Signals from the membrane electrode biosensor monitor the drug flow rate of permeant being transported through the skin as well as the membrane electrode. The pump/titration regulator receives these signals from the membrane biosensor to regulate exact controlled increments of the permeant being delivered to the surface of the skin with an even flow pressure distribution in the electrophoretic tubing and membrane electrodes in the cuff delivery system. Alternatively, a roller clamp can be used to clamp I.V. tubing to control the flow of the pharmaceutical permeant.

In view of the above, it should be apparent that the present invention provides many advantages and overcomes many of the shortcomings and disadvantages of the prior art, while providing an improved apparatus.

Additional features and advantages of the invention will become apparent from the following drawings and description.

BRIEF DESCRIPTION OF THE DRAWINGS

For a better understanding of the invention with regard to the embodiments thereof, reference is made to the accompanying drawings, in which like numerals designate corresponding elements or sections throughout, and in which.

DETAILED DESCRIPTION OF THE PREFERRED EMBODIMENT

With specific reference now to the figures in detail, it is stressed that the particulars shown are by way of example and for the purpose of illustrative discussion on the preferred embodiments of the present invention only, and are presented in the cause of providing what is believed to be the most useful description principles and conceptual aspects of the invention, based upon the medical literature. In this regard, no attempt is made to show structural aspects of the invention in more detail than is necessary for a fundamental understanding of the invention, the description taken with the drawings making it apparent to those skilled in the art how the several forms of the invention may be embodied in practice.

Figure 1:
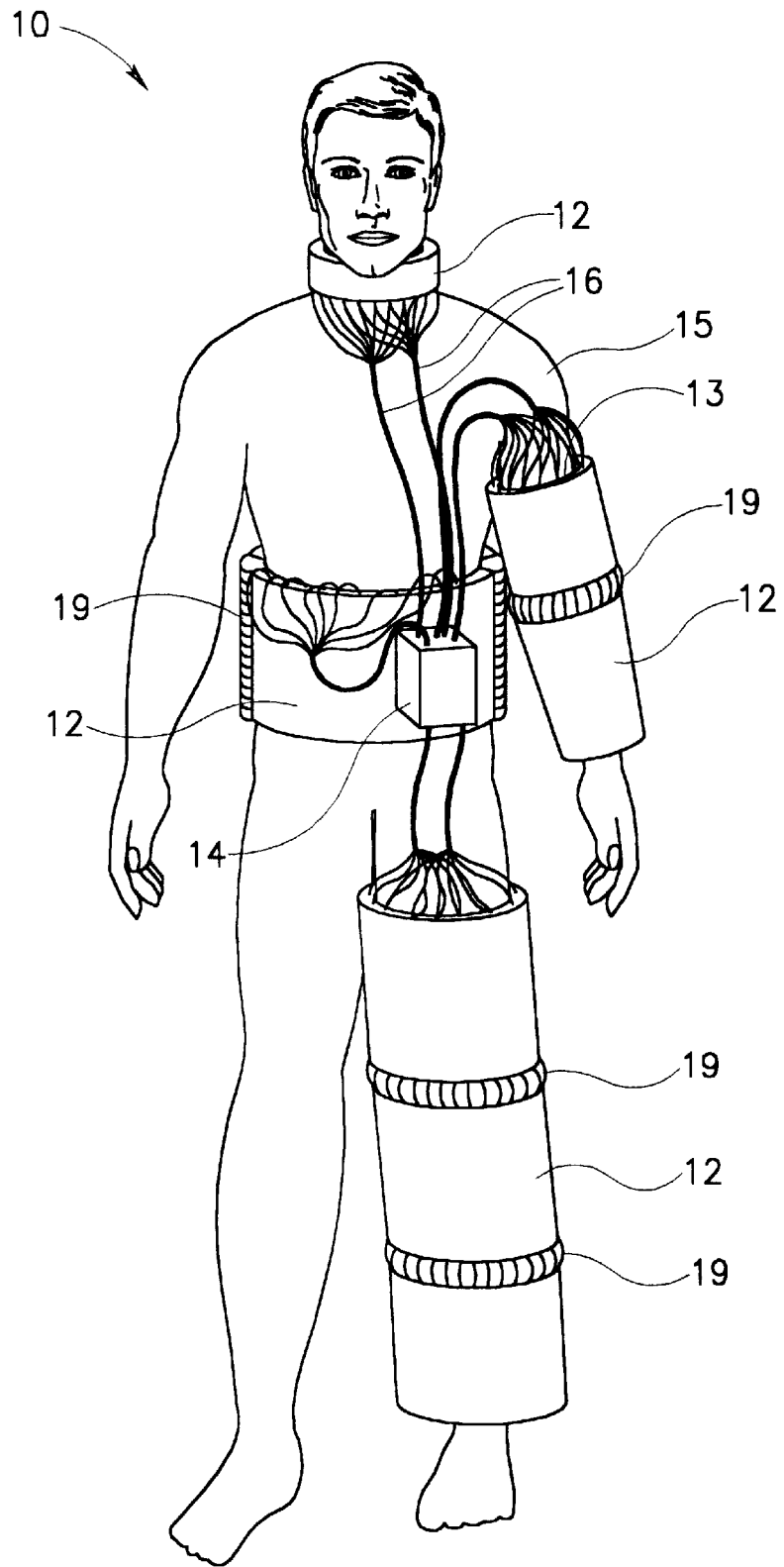
FIG. 1 is a front elevational view pictorially illustrating the electrophoretic cuff apparatus of the invention as applied to selected portions of the human body, including neck, arm, lower back and leg.

Referring now to FIG. 1, there is illustrated a pictorial representation of an electrophoretic cuff apparatus 10 in accordance with this invention. The electrophoretic cuff apparatus 10 is typically shown at selected anatomical locations on a human body.

The apparatus 10 is comprised of a flexible cuff 12 for wrapping around a body part or limb, a portable operating console 14 that incorporates a power supply source and a cable harness 16 for conductively coupling the console 14 to the cuff wrap 12.

Figure 3:
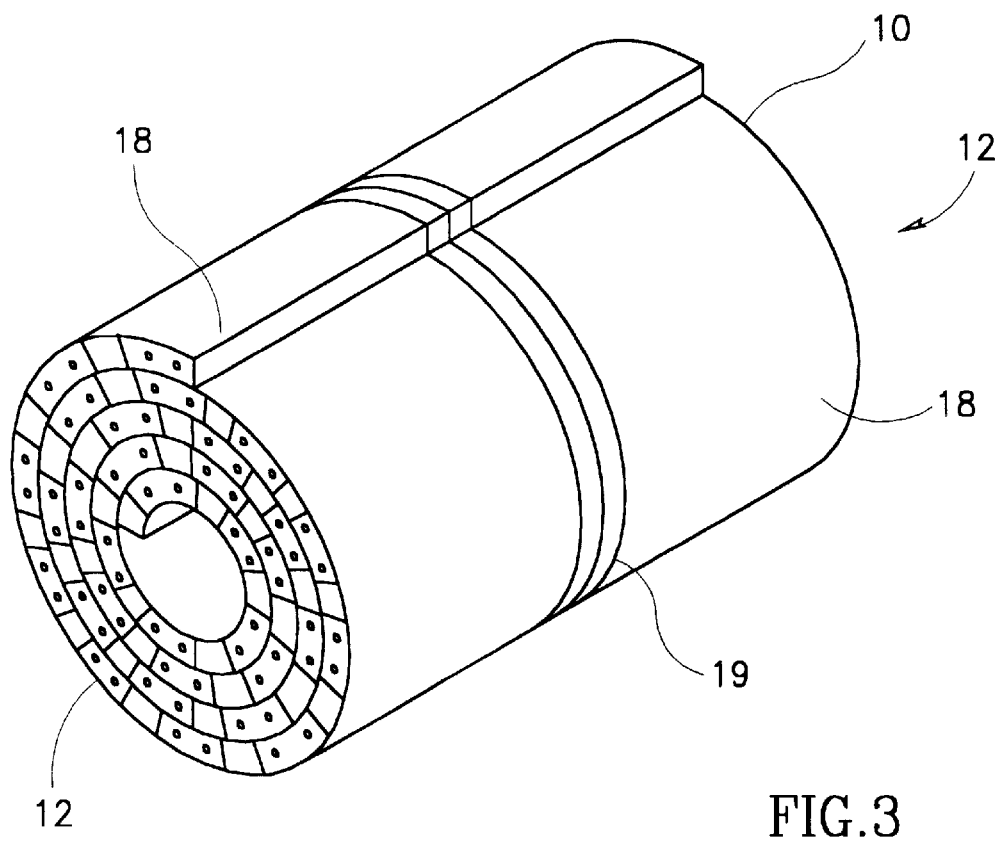
FIG. 3 is a perspective view of a portion of a patch connected to other patches forming a cuff in a stored configuration.
Figure 4A:
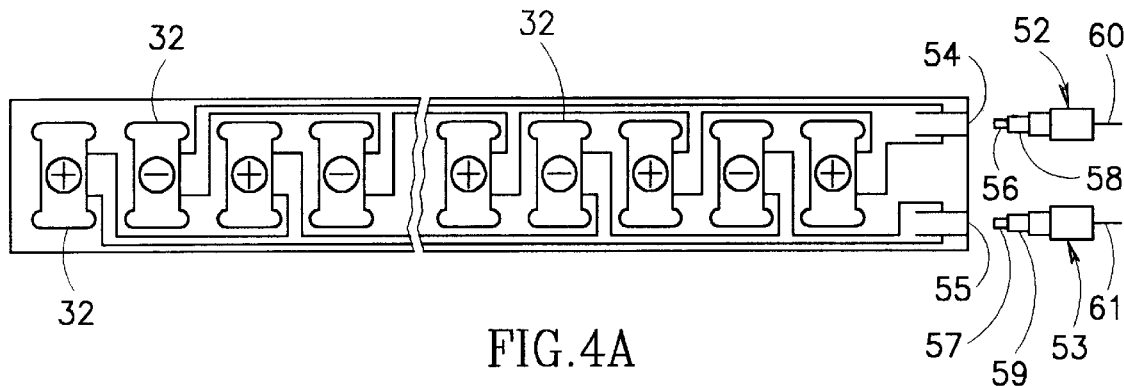
FIG. 4a is an elevational view, in enlarged scale, of a portion of the applicator cuff, showing the electrical circuitry for energizing the electrode applicator pads.

Flexible cuff wrap 12, as best shown in FIGS. 1 and 3, is fabricated from a plastic and/or canvas garment-like fabric, having linked patches 18 connected by Velcro strapping 19 as a closure for securing cuff wrap 12 against afflicted areas on the patient's body, for example, as shown in FIG. 1. Linked patches 18 provide the required flexibility when applied around or on a body part, and are compliant when attached to another set of linked patches 18 by Velcro strapping 19 and connected by electrical connector plugs 52, 53 (FIG. 4*a*) and fluid-flow connectors 21 (FIG. 4*c*).

Figure 2:
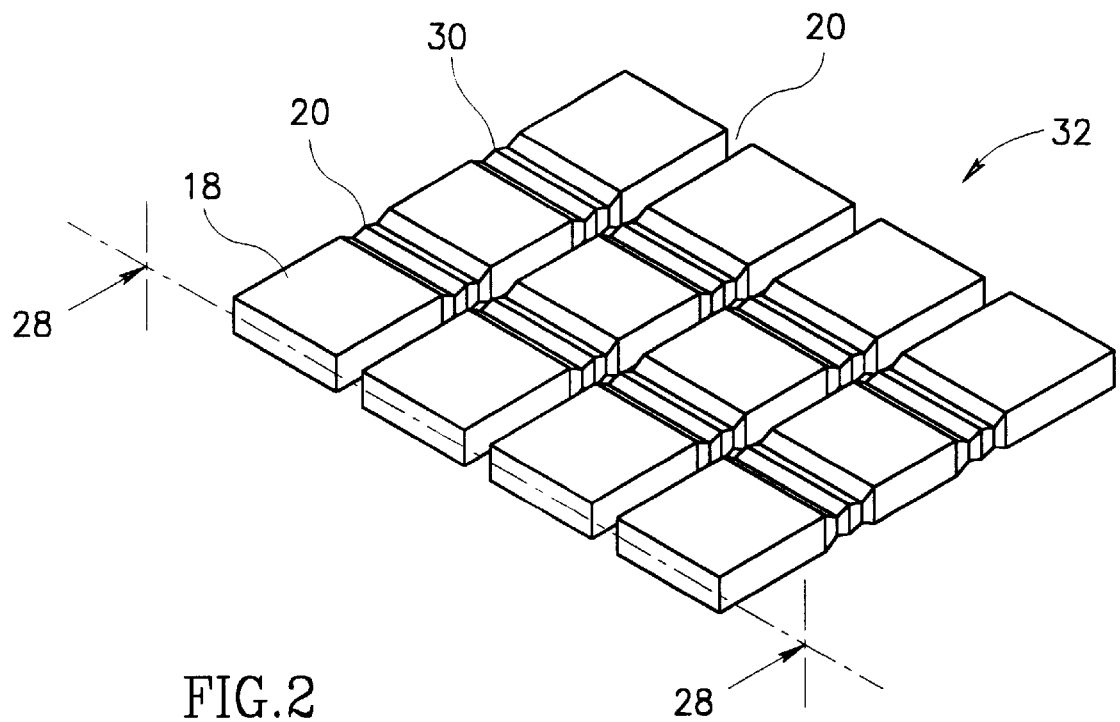
FIG. 2 is a perspective view of a portion of an applicator patch in conjunction with the apparatus of the invention illustrating a grid of electrode applicator pads.

In FIG. 2, a plurality of porous electrode applicator pads 32 which are made of polymer or equivalent materials, are positioned within each patch 18 such that a longitudinal axis 28 of the electrode applicator pads 32 is perpendicular to a transverse axis 30 of cuff wrap 12. Electrode applicator pads 32 function as a porous electroconductive membrane layer. Contact surface 13 of cuff wrap 12 is intended for placement contiguous to the patient's skin 15. By way of example, electrode applicator pads 32, such as shown in FIG. 4, are rectangular, approximately ⅜ in. on each side and are spaced apart at point 20 approximately 2:1 ratio center to center, to provide about four electrode applicator pads 32 per square inch within the cuff wrap 12.

Figure 5:
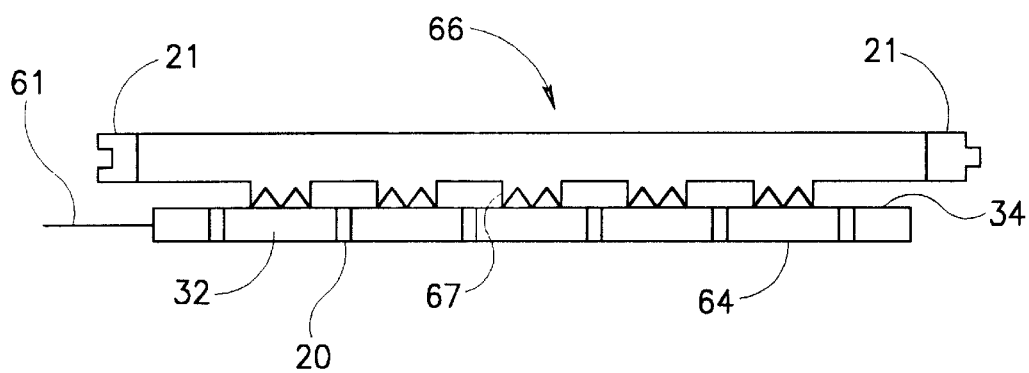
FIG. 5 shows a schematic drawing of a side view cross-section, showing the electrodes and supply tubes for delivering the fluid medium to the electrode applicator pads via a system of branching ducts.

Furthermore, electrode applicator pads 32 can be embedded in the plastic material during the manufacturing process, and are thus secured in place by the surrounding plastic material. Alternatively, electrophoretic tubing 66 and tubing connectors 21 pass on top of, and are superior to, surface 34 of electrode applicator pads 32, simultaneously as they connect with the electrodes via duct system 67 as shown in FIG. 5.

Further in connection with the fabrication of cuff wrap 12, it should be observed that before electrodes 32 are fixed into position, inside wiring 61 and electrophoretic tubing 66 are placed against the inside face of a waterproof substrate and/or canvas-like fabric forming the apparatus matrix, to prevent "leakage" of medicated or non-medicated fluid outside the aforementioned cuff.

Figure 4B:
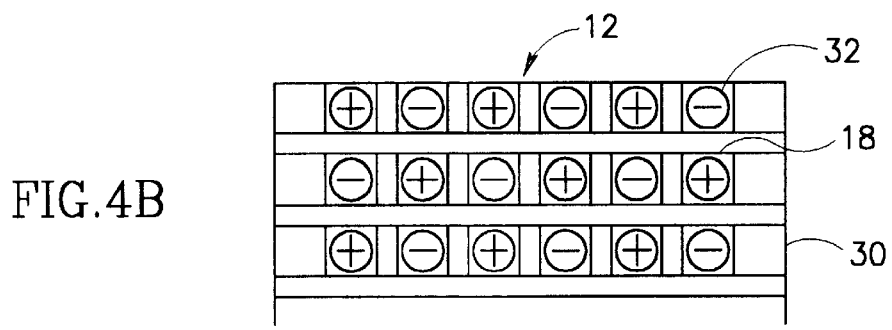
FIG. 4b is a top view of a portion of an applicator wrap used in conjunction with the apparatus of the invention, illustrating a "checkerboard" pattern of positive and negative electrically charged electrodes.
Figure 4C:
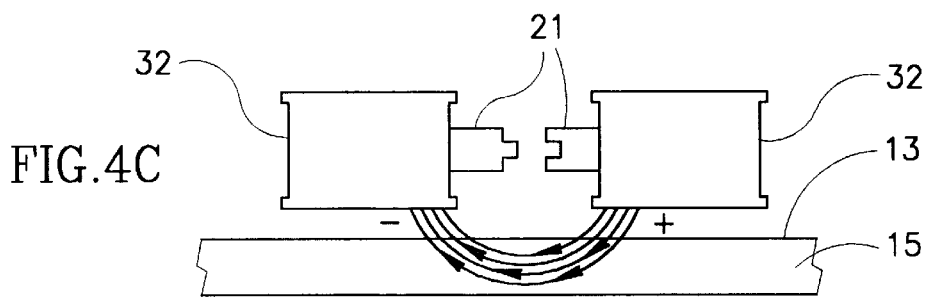
FIG. 4c is an elevational view showing the combined lines of positive and negative electron flow, or the electrical charge of opposite polarity associated with the apparatus.

Referring once again to electrode applicator pads 32, it will be noted that in FIG. 4 the wiring sequence for each electrode applicator pad 32 provides for a current flow through adjacent electrodes to thereby generate a "checkerboard" of electrical currents of alternate polarities, as graphically depicted in FIG. 4*b*. This is accomplished by conductively coupling the wiring in two circuits, as will be further described herein. It will be appreciated by those skilled in the art that the inside wiring within patch 18 can be comprised of a modified electrode applicator pad comprising an electroconductive polymer membrane. A wire harness 16, as shown in FIG. 1, is conductively coupled to patches 18 by a set of (two-conductor) connector plugs 52, 53 that are accommodatingly received within a corresponding set of sockets 54, 55.

Referring to FIG. 4*a*, it will be seen that the set of plugs 52, 53 contains two conductors comprised of portions 56, 58, 60 and 57, 59, 61 respectively. The conductor portions 56, 58 and 57, 59, when inserted within the respective sockets 54, 55 complete circuits for energizing the electrodes. As seen in FIG. 4*c*, it will be noted that when the current flows in a clockwise direction in the electrode applicator pads 32 in one circuit defined by plug 52, the current will correspondingly flow in a counterclockwise direction through the electrodes within the other circuit defined by plug 53.

Figure 6:
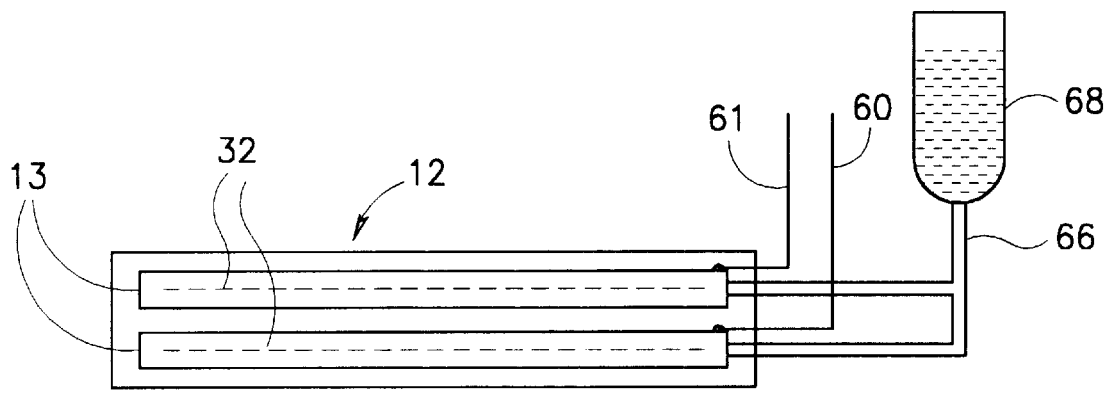
FIG. 6 is a cross-sectional view of an electrophoretic pharmaceutical delivery system with a fluid reservoir connected to the apparatus.

In FIG. 6 there is shown an electrophoretic pharmaceutical delivery system with fluid reservoir 68. Electrophoretic cuff 10 can induce a pharmaceutical fluid flow when simultaneously placed under a cast or brace with additional treatment modalities of electrostimulation. In addition, pain sedation can be provided by nerve stimulation analgesia, and galvanic muscle strengthening can be provided by producing muscle contraction that deters the onset of atrophy in a body part. The electrostimulation regimen is also effective for reversing the degenerative effects of atrophy.

This aspect of the invention uses electrode applicator pads 32 as conductive stimulator pads. Electrode applicator pads 32 are applied to contact surface 13 of cuff wrap 12. Conductors 60, 61 provide electrode applicator pads 32 with opposite charges of DC current. When cuff wrap 12 is placed on the patient, electrode applicator pads 32 are in direct contact with the skin surface.

The previously described muscular electrostimulation and interferential microcurrent therapy can be used independently or in combination with the electrophoretic therapy delivery system.

The purpose of the iontophoresis is to utilize an electrical field to influence the transfer and metabolism of the drug medium into the patient's body, as shown in FIG. 6. For this purpose, electrode applicator pads 32 include a porous material that is connected by a network of tubing 66 supplied with a selected drug medium from reservoir 68 through a gravity feed system. It should be further noted that electrode applicator pads 32 will at all times be oppositely charged. In operation, electrode applicator pads 32 provide the function of receiving the pharmaceutical medium from branch tubing 66. The fluid medium is distributed throughout pads 32 by capillary action.

Figure 7:
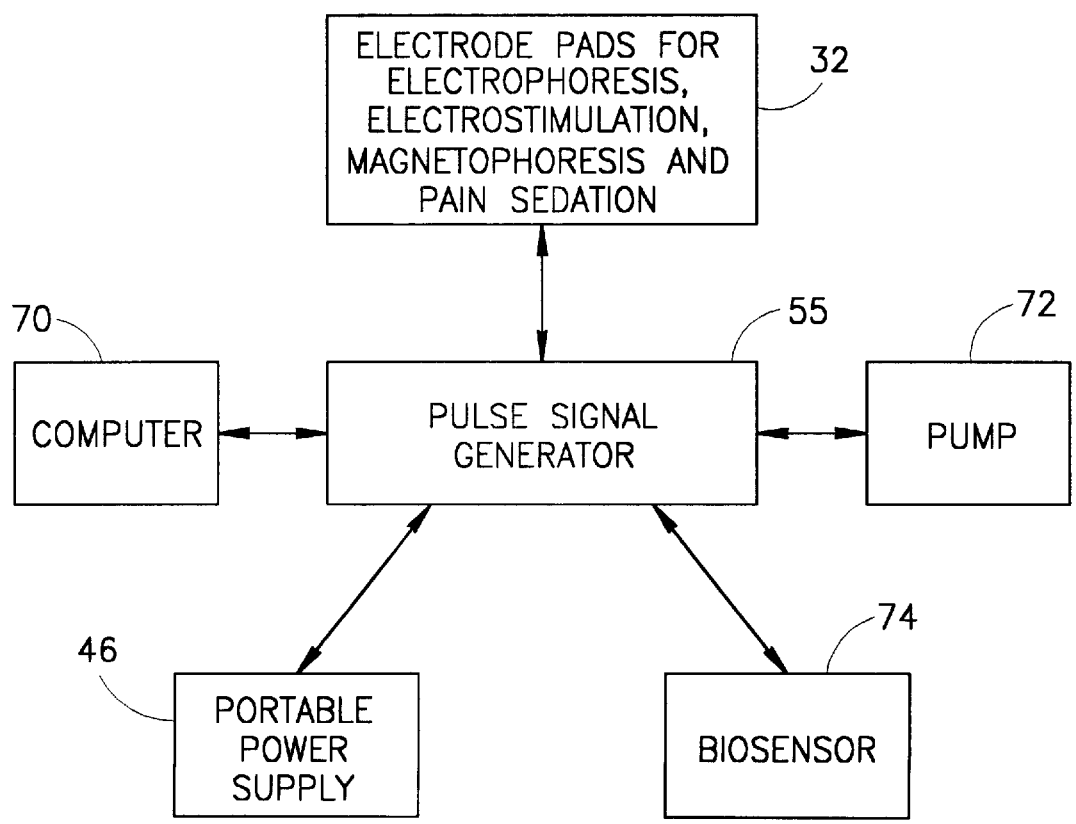
FIG. 7 is a block diagram of the invention showing the electrode applicator pads within the system components.

As shown in FIG. 7, the application of the electrical current from power supply 46 provides an ionization effect producing a more effective delivery path to the patient. This is particularly advantageous when a conventional cast or brace has been placed over electrophoretic cuff apparatus 10 and thus the afflicted area is otherwise inaccessible to direct drug therapy.

With regard to the electrophoretic pharmaceutical delivery system, a computerized chip and monitor 70 in a fluid distribution system monitors and supplies the medicated fluid from external bag reservoir 68 at various desired titration rates of ml/second through regulating pump 72. Rate of flow needed is determined by biosensor 74, and regulates fluid flow to increase efficiency to perform iontophoresis. Pulse signal generator 55 receives power from power supply 46 to provide pulses to electrode applicator pads 32 for electrostimulation, magnetophoresis, electrophoresis and pain sedation.

Figure 8:
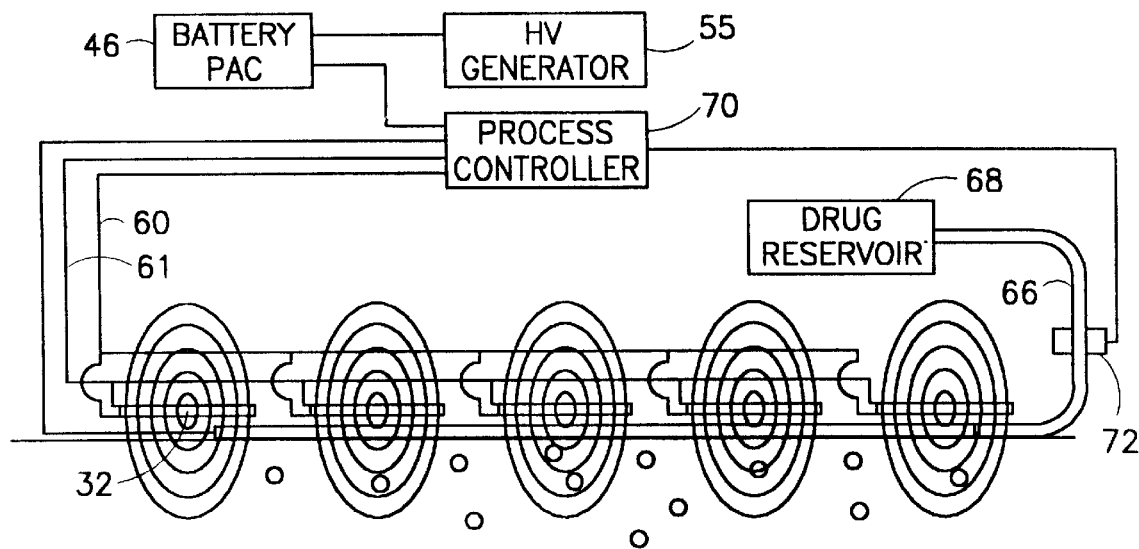
FIG. 8 shows a schematic drawing of a side view cross-section showing the electromagnetic electrodes to create the drive mechanism for magnetophoresis.

Referring now to FIG. 8, there is shown a schematic drawing in which electrodes 32 are supplied as electromagnetic electrodes and are arranged to create the drive mechanism for magnetophoresis. Magnetic fields generate an electrical field within the tissue which is perpendicular to the magnetic field. This magnifies the electrical field strength, thereby increasing the penetration factor without increasing the externally applied current. This method produces a homogeneous potential layer.

When the electrocurrent drivers are combined with electromagnetic fields with an electrophoretic current, the driving force to increase drug delivery through membranes is greatly enhanced. The effects of pulsed electromagnetic fields (PEMF) are explained by the changes in the distribution of electrostatic charges near the membrane proteinprotein binding sites. In the present invention, the process of combining PEMF and electric currents for transdermal drug delivery through a membrane electrode carrier has been termed "electro-infusion" (c). The electro-infusion technique creates greater absorption and depth penetration of a permeant to a target area. In addition the use of PEMF's assists in localization of the drug to a specific target area. When a multiple array of membrane electrodes are arranged on an anatomical area in a cylindrical fashion perpendicular to the SC forming cuff apparatus 10, a high rate of drug delivery to a specific treatment area will result.

By having a multiple arrangement of membrane electrodes 32 delivering the permeant over a large circumference, an alternating sequence is consecutively changing the infiltration area. The end result of this is avoidance of skin irritation. The living tissue is protected while ionic shift is eliminated, allowing increased penetration of ions. It is possible to transfer simultaneously several types of permeants which have inverse polarities.

Preferred power supply 46 is an electrochemical cell such as a commercially available nickel cadmium or lithium 9 volt rechargable battery. The battery is housed within console 14. Pulse generator 55 is included within console 14. Generator 55 supplies DC electrical power for electrostimulation and for the electrophoretic pharmaceutical delivery system.

It should be noted that pulse generator 55 provides a direct current of low frequency having sinusoidal and trapezoidal waveform pulses at between 1–200 Hertz. It should be understood, however, that pulse generator 55 can be modulated in accordance with the desired electrostimulation therapy.

The signals utilized in connection with the electrophoretic system include DC current modulation having trapezoidal, square and sinusoidal wave pulses from 0–50 volts with alternating and continuous pulses modulated at between 1 to 200 Hertz and the electrical current ranging from 0–500 mA, with a current range from 0–15 mA responsible to perform iontophoresis. For iontophoresis, the mode can vary 50% on, 50% off or as desired. For neuromuscular stimulation, the pulses have a 20–30% off and 70–80% on timing for maximum effectiveness.

Figure 9:
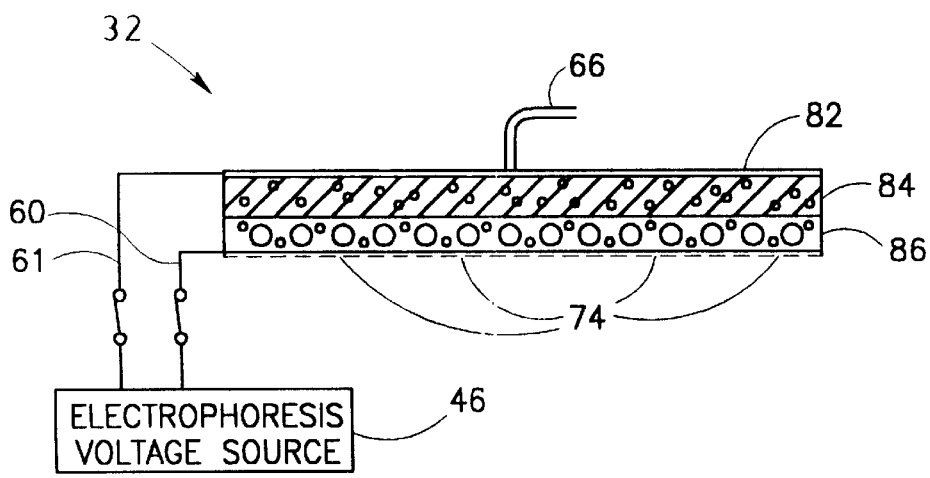
FIG. 9 is a cross-section showing the electrode applicator pads divided into functional sections.

Referring now to FIG. 9, there is shown a cross-sectional view of electrode applicator pad 32. Electrode applicator pad 32 comprises a three layer structure, including sealant 82, microtitration foam 84 and membrane 86. Sealant 82 is on the superior aspect and connects with electrophoretic tubing supply 66. Inferior to sealant 82 is microtitration foam 84. Foam 84 assists in permeant delivery timing and prevents excess permeant from running off. The foam may be cultured, dehydrated and/or gamma irradiated to ensure that biological contamination is prevented. The foam binds to membrane 86.

Membrane 86 is formed of an electrically woven fabric which is treated with antibiotic and antifungal chemicals to prevent biological contamination. The membrane itself is commercially available (for example, IonClad R1010, R1030, R4010 or R4030 from Pall Corp., Port Washington, N.Y.) and made of polymers that have ultra-filtration properties of 100,000 to 200,000 molecular weight cut-off and 2 nm to 1 μm pore size to accomodate drugs of a high molecular weight. Membrane 86 can also be provided as an electroconductive porous polymer or co-polymer. The large molecular weight cut-off allows drugs such as insulin (MW 6000), heparin (MW 6000–30,000), plasma factors (MW over 50,000) and anti-cancer drugs to be used with the system. Multiple drug delivery of large and small size drugs is possible. Membrane 86 acts as a reservoir and is encased in a barrier to prevent uncontrolled leakage of the drug. Membrane 86 is electro-conductive to provide for electrophoresis and other treatment modalities.

In addition, membrane 86 is provided with a substance on the epidermal delivery layer to cause hyper-permeability of the permeant through the stratum corneum (SC) of the skin and into deeper body tissue layers. The SC is a thin layer of highly resistant tissue with the underlying viable dermis exhibiting a much lower resistance. The membrane is laced with acetylcholine, epinepherine or other stimulants to enhance permeability through the SC.

Figure 10:
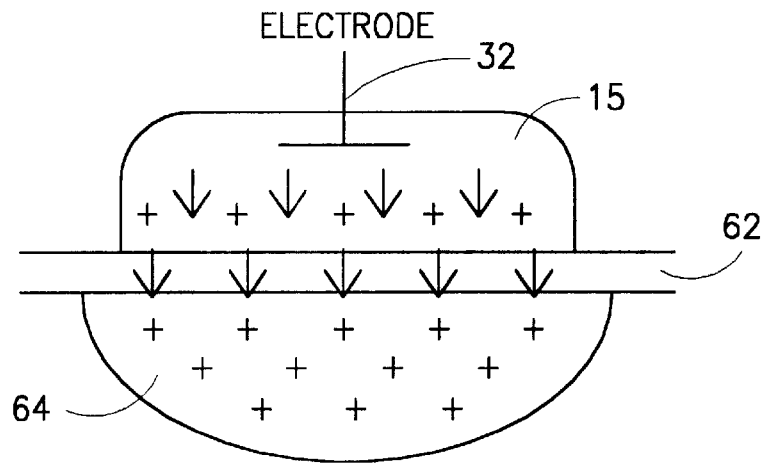
FIG. 10 is a diagram showing the flow of permeant through the skin surface.

Biosensors 74 are disposed inferior to membrane 86, on the skin surface, and are connected to the computerized titration system to sense the flow rate of permeant through the SC. FIG. 10 depicts the flow of permeant through the skin surface 15 to an area 64 of increased concentration, in response to electrode applicator pad 32. Dry skin has a low resistance (as low as 2.5 microohms/cm$^2$), and SC 62, having a lower water content (20%) than other epidermal cells (about 70%), represents a less conductive medium. Penetration through the SC is the rate determining step in transdermal drug absorption. This biological phenomenon has been the source of variability in the determination of appropriate dosage for ion transfer. The adjustment of the dosage parameters is essential to provide optimal transfer of the ionized medication while insuring the safety of the patient.

Biosensor 74 can be constructed to comprise three electrodes which are saturated with normal saline. The first biosensor electrode serves as the reference electrode and is situated far from the treatment area. The second biosensor electrode is localized exactly above the treatment area and is the analyzing electrode. The third biosensor electrode is near the reference electrode for comparison purposes. A sensitive milllivolt meter measures the voltage between the reference electrode and the comparison electrode. Then the difference is measured between the reference electrode and the analyzing electrode. The difference in millivolts between the two measurements is the actual concentration gradient. Using the skin resistance value the final value can be extrapolated. The system needs to be calibrated for each drug.

Figure 11:
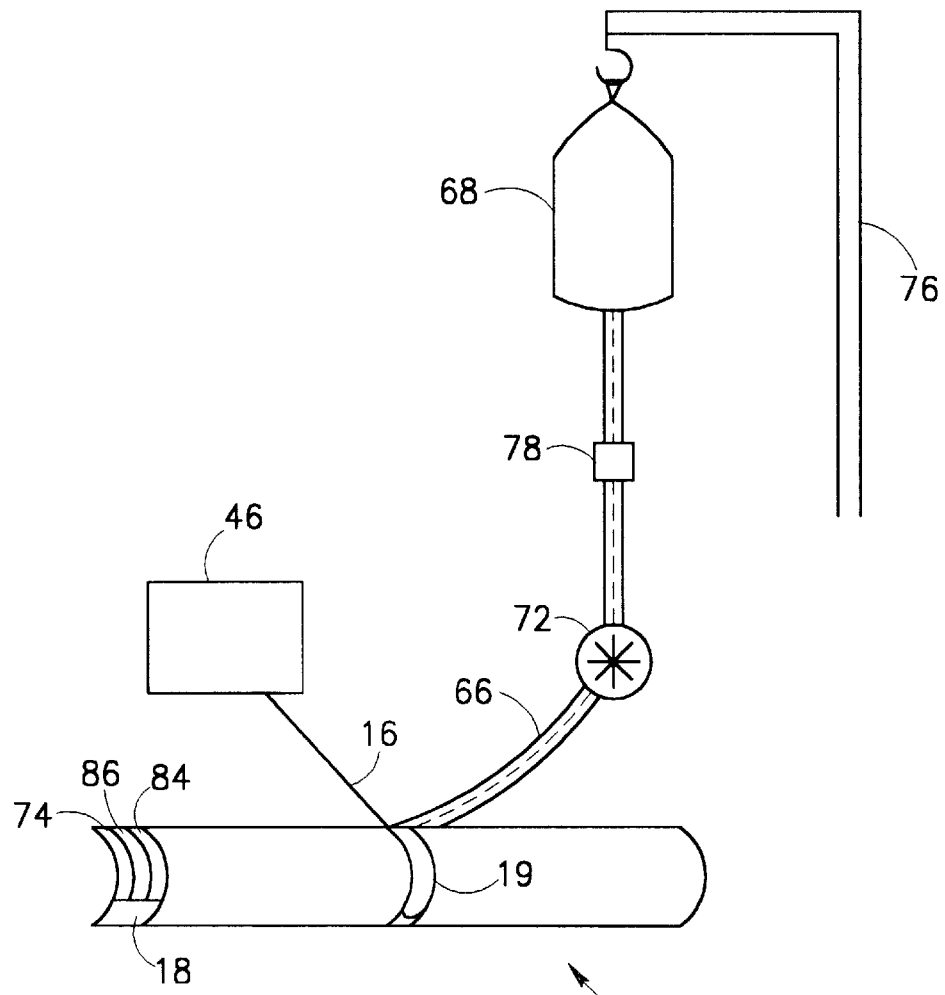
FIG. 11 is a diagram showing an assembly of the complete drug delivery system.

FIG. 11 shows an overview of a preferred embodiment of apparatus 10 as used with a standard IV drip bag and pole stand. Stand 76 holds reservoir 68, allowing fluid to drip through drip chamber 78 to pump and titration regulator 72. Tubing 66 leads the fluid into cuff wrap 12 to patches 18. Harness wires 16 from power source 46, also leading into patches 18 provide electricity for electrophoresis, magnetophoresis, electrostimulation and pain sedation. Patches 18 are supplied with electrode applicator pads 32 which are comprised of sealant 82, microtitration foam 84, porous electro-conductive membrane 86 and are equipped with biosensors 74.

It should be observed that this treatment mode also provides, as an adjunct, transcutaneous nerve stimulation for pain sedation. In this regard, the transcutaneous nerve stimulation can be effected concurrently with or independently of the iontophoretic drug therapy.

It should be further observed that low frequency, low intensity interferential currents are used to treat edema or swelling associated with injuries and can be used in electrodes provided within this system.

The apparatus forms a cuff that allows patients with atrophy to perform passive and active exercise while wearing it.

It should also be further observed that the network of reservoir and tubing can be optionally used to distribute inert liquids that provide thermal fluid therapy, hot or cold, to a target area within the patch or cuff if so desired. A temperature gauge attached to the reservoir measures the temperature in Celsius and/or Farenheit. It is well known in the literature that temperature has an influence on transdermal transport of drugs during iontophoresis.

It should thus be apparent that a clinician or patient can choose desired options of the aforementioned therapies singularly or in combination using operating console 14.

It will be evident to those skilled in the art that the apparatus is not limited to the details of the foregoing illustrated embodiments and that the present may be embodies in their specific forms without departing from the spirit or essential attributes thereof.

The present embodiment is therefore to be considered in all respects as illustrative and not in a restrictive sense. The scope of the being indicated by the appended claims rather than by the foregoing description and all changes which come within the meaning and range of equivalency of the claims are therefore intended to be embraced therein.

I claim:

1. An electrophoretic cuff apparatus comprising:
    an applicator wrap of single or multiple connecting patch units each containing a plurality of electrophoretic electrode applicator pads;
    means for simultaneously generating an electric current in each of said applicator pads; and
    a network of tubing adjacent to a surface of said applicator pads for delivering a selected pharmaceutical medium to said applicator pads, said applicator pads being selectively energized by said electric current for providing drug treatment therapy, wherein said applicator pads each comprise:
        a layer of foam for retaining a quantity of said pharmaceutical medium therein;
        an electroconductive membrane disposed under said foam layer though which said pharmaceutical medium passes; and
        a biosensor integrated within said electroconductive membrane for sensing a quantity of said pharmaceutical medium passing therethrough and developing a responsive signal.

2. The apparatus of claim 1 wherein said electrophoretic electrode applicator pads are connected to a slow drip liquid drug reservoir through a pump connected to said electrophoretic tubing with a system of duct distribution to each and every individual porous electrode applicator pad to deliver a drug through the skin and surface tissues.

3. The apparatus of claim 2 further comprising a computerized control device for regulating flow from said slow drip liquid reservoir through said pump to said electrophoretic tubing, in accordance with said responsive signal.

4. The apparatus of claim 1 wherein said biosensor comprises:
    a set of spaced apart electrode plates, comprising a reference electrode, an analyzing electrode, and a comparison electrode, said analyzing electrode disposed proximate a treatment area, said reference electrode disposed away from said treatment area, and said comparison electrode disposed between said analyzing and reference electrodes closer to said reference electrode, said responsive signal being a voltage representing the difference in voltage differentials measured between said reference electrode and each of said analyzing and comparison electrodes.

5. The apparatus of claim 1 further comprising regulation means for controlling passage of said pharmaceutical medium through said membrane in accordance with said responsive signal, to regulate and permeate said pharmaceutical medium in a treatment area by active transport transdermally.

6. The apparatus of claim 1 in which said electric current generates magnetic and electric fields providing a drive mechanism for transdermal magnetophoresis and iontophoresis of said pharmaceutical medium.

7. The apparatus of claim 6 in which said electric current is combined with said electromagnetic field to develop tranderdmal electro-infusion of said pharmaceutical medium.

8. The apparatus of claim 1 in which said pharmaceutical medium is a chemotherapy drug for electrochemotherapy.

9. The apparatus of claim 1 in which said electric current provides electrostimulation therapy.

10. A drug delivery system comprising:
    an electrophoretic cuff apparatus comprising:
        an applicator wrap of single or multiple connecting patch units each containing a plurality of electrophoretic electrode applicator pads;
        means for simultaneously generating an electric current in each of said applicator pads; and
        a network of tubing adjacent to a surface of said applicator pads for delivering a selected pharmaceutical medium to said applicator pads, said applicator pads being selectively energized by said electric current for providing drug treatment therapy,
        wherein said applicator pads each comprise:
            a layer of foam for retaining a quantity of said pharmaceutical medium therein;
            an electroconductive membrane disposed under said foam layer though which said pharmaceutical medium passes; and
            a biosensor integrated within said electroconductive membrane for sensing a quantity of said pharmaceutical medium passing therethrough and developing a responsive signal,
        a pump connected to said network of tubing, and
        regulation means connected to said pump for controlling the flow of said pharmaceutical medium in accordance with said responsive signal.

11. The apparatus of claim 10 wherein said regulation means comprises a computerized control device.

12. The electrophoretic cuff apparatus as claimed in claim 11, wherein said computerized control device comprises a display readout of a flow rate of said pharmaceutical medium.

13. A method of providing electrophoretic drug treatment therapy comprising the steps of:
    providing an electrophoretic cuff apparatus comprising:
        an applicator wrap of single or multiple connecting patch units containing a plurality of electrophoretic electrode applicator pads;
        means for simultaneously generating an electric current in each of said applicator pads; and
        a network of tubing adjacent to a surface of said applicator pads,
        wherein said applicator pads each comprise:
            a layer of foam for retaining a quantity of said pharmaceutical medium therein;
            an electroconductive membrane disposed under said foam layer through which said pharmaceutical medium passes; and
            a biosensor integrated within said electroconductive membrane for sensing a quantity of said pharmaceutical medium passing therethrough and developing a responsive signal, delivering a selected pharmaceutical medium to said applicator pads, said applicator pads being connected to a controlled slow drip liquid reservoir through said network of tubing with a system of duct distribution to each and every individual applicator pad; and selectively energizing said applicator pads by said electric current to provide said drug treatment therapy through the skin and surface tissues.

14. The method of claim 13 wherein said delivering step is performed by a computerized control device in accordance with said responsive signal.

15. The method of claim 13 wherein said step of selectively energizing said applicator pads establishes at least one of anode and cathode drug delivery modes.

16. The method of claim 13 wherein said step of selective energizing said applicator pads provides a DC current modulated in at least one of trapezoidal, square and sinusoidal wave pulses from 0–50 volts with alternating and continuous wave pulses modulated between 50 and 200 Hz and the electrical current ranging from 0 to 50 mA, within a current range of 0 to 15 mA.

17. The method of claim 13 wherein said step of selective energizing said applicator pads provides a DC electromagnetic current modulated in a format of at least one of trapezoidal, square and sinusoidal wave pulses from 0–50 volts with alternating and continuous pulses modulated between 0 to 200 Hz and the electrical current ranging from 0 to 50 mA, within a gauss range from 0–100 Gauss.

18. The method of claim 16, wherein said pulses are generated as at least one of two types, combined and individual.

19. The method of claim 17, wherein said pulses are generated as at least one of two types, combined and individual.

20. The method of claim 13 further comprising the step of providing a computerized control device for regulating flow from said slow drip liquid reservoir through said tubing.

* * * * *